United States Patent [19]

Hansen et al.

[11] Patent Number: 5,763,426
[45] Date of Patent: Jun. 9, 1998

[54] NEW CRYSTALLINE FORM OF A VITAMIN D ANALOGUE

[75] Inventors: Erik Torngaard Hansen, Fredensborg; Niels Smidt Rastrup Andersen, Vanløse; Lene Hoffmeyer Ringborg, Brønshøj, all of Denmark

[73] Assignee: Leo Pharmaceutical Products Ltd., Ballerup, Germany

[21] Appl. No.: 491,892

[22] PCT Filed: Jan. 15, 1993

[86] PCT No.: PCT/DK94/00011

§ 371 Date: Jul. 14, 1995

§ 102(e) Date: Jul. 14, 1995

[87] PCT Pub. No.: WO94/15912

PCT Pub. Date: Jul. 21, 1994

[30] Foreign Application Priority Data

Jan. 15, 1993 [GB] United Kingdom ............... 9300763

[51] Int. Cl.⁶ .................. A61K 31/59; C07C 401/00
[52] U.S. Cl. ............................... 574/167; 552/653
[58] Field of Search .................. 552/653; 514/167

[56] References Cited

U.S. PATENT DOCUMENTS 4,435,325   3/1984  Jolly et al. ................ 260/397.2
4,866,048   9/1989  Calverley et al. ............. 514/167

FOREIGN PATENT DOCUMENTS 87 00834   2/1987   WIPO .

OTHER PUBLICATIONS

Thavarajah, et al: "1,25(OH)₂D₃ and Calcipotriol (MC903) Have Similar Effects on the Induction of Osteoclast–Like Cell Formation in Human Bone Marrow Cultures", Biochemical and Biophysical Research Commnications., vol. 171, No. 3, Sep. 28, 1990, pp. 1056–1063.

Bagot , et al: "Immunosuppressive Effects of 1,25–Dihyrixyvitamin D3 Analog (Calcipotriol) on Epidermal Cells", Chemical Abstracts, vol. 119, No. 5, Aug. 2, 1993, abstract No. 41719, p. 182, col. 1, see abstract & Proc.Workshop Vitam.D (8th) 1991 pp. 518–519.

Braeutigam, et al: "Effects of Calcipotroil (MC903) and Calcitriol After Topical Application on the Skin of Hairless Rats. Much Lower Effect of Calcipotriol on Systemic Calcium Homeostasis", Chemical Abstracts vol. 117, No. 21, Nov. 23, 1992, abstract #205159, p. 93, col. 1, see abstract & Skin Pharmacol. vol. 5, No. 2, 1992, pp. 87–92.

Kragblle et al: "Vitamin D Analogs in The Treatment of Psoriasis", Chemical Abstracts, vol. 116, No. 25, Jun. 22, 1992, abstract No. 248622, p. 90, col 1, see abstract & J.Cell.Biochem. vol. 49, No. 1, 1992, pp. 46–52.

Larsen, et al: "Structure and Absolute Configuration of a Monohydrate of Calcipotriol, (1.alpha.,3,5Z,7E,22E,24S)–24–Cyclopropyl–9,10–secochola–5,7 10(19),22–tetraene–1,3,24–triol", Acta Crystallographica, Section C, Crystal Structure Communications, vol. C49, No. 3, 1993, pp. 618–621, se the hwole document.

Primary Examiner—José G. Dees
Assistant Examiner—Barbara Badio
Attorney, Agent, or Firm—Pillsbury Madison & Sutro LLP

[57] ABSTRACT

The present invention relates to calcipotriol hydrate—a new crystalline form of calcipotriol—with superior technical properties and with superior stability.

7 Claims, No Drawings

NEW CRYSTALLINE FORM OF A VITAMIN D ANALOGUE

This application is a 371 of PCT/DK94/00011 filed Jan. 7, 1994.

The present invention relates to calcipotriol, hydrate—a new crystalline form of calcipotriol—with superior technical properties e.g. in the manufacture of crystal suspension formulations, and with superior stability properties.

Calcipotriol (INN) (calcipotriene (USAN), (1α,3β,5Z, 7E,22E,24S)-24-Cyclopropyl-9,10-secochola-5,7,10(19), 22-tetraene-1,3,24-triol) is described in International patent application No. PCT/DK86/00081, filing date 14th Jul. 1986, publication No. WO 87/00834.

Calcipotriol possesses a remarkable profile of biological activity which has proved very useful e.g. in the topical treatment of psoriasis.

Due to the poor stability of calcipotriol in certain solutions it is in some formulations, in particular in creams and gels, preferred to use crystal suspensions.

In order to prepare suitable crystal suspension formulations it is mandatory to be able to control the crystal size, this parameter being important with regard to obtaining a reproducible release of the active compound from the formulation. The crystalline bulk drug is usually subjected to micronization or to a wet milling process in order to reduce the crystal size before the final suspension formulation is prepared.

In the case of calcipotriol a wet ball milling process has been used. However, it has turned out to be technically difficult to perform this process when using the anhydrous crystal form described in WO 87/00834. These crystals are not easily wetted and during the milling process they develop a stable foam which results in difficulties in obtaining a suitable small and uniform particle size.

It has now surprisingly been found that these technical problems can be avoided when a hitherto unknown crystalline form of calcipotriol, i.e. calcipotriol, hydrate, is used instead of the known anhydrous form. The hydrate is technically superior to the anhydrate; it is easily wetted and the wet ball milling process is running smoothly.

This novel product is the monohydrate of calcipotriol which is perfectly crystalline, stable and well suited for its use in modern therapy.

Stability studies have demonstrated that calcipotriol, hydrate is surprisingly stable, and this is illustrated by stability data at 40° C.

The anhydrous form of calcipotriol shows a considerable degree of decomposition at this temperature and more than 30% degradation is seen after 12 months storage.

In contrast the compound of the present invention, calcipotriol hydrate, shows no degradation after 12 months storage at 40° C.

Calcipotriol, monohydrate may be prepared by dissolving crystalline or non-crystalline calcipotriol in an organic solvent, e.g. ethyl acetate or acetone, followed by the addition of water and optionally a non polar solvent, e.g. hexane.

Calcipotriol, monohydrate shall form part of pharmaceutical preparations for topical use, such as creams, ointments, solutions, lotions or gels. The concentration of the active ingredient will generally be between 1 and 100 µg/g.

The formulations will be applied one or more times daily.

The formulations prepared according to the present invention comprise the active compound in association with a pharmaceutically acceptable vehicle and optionally other therapeutic ingredient(s). The vehicle(s) must be "acceptable" in the sense of being compatible with the other ingredients of the preparations and not deleterious to the recipient thereof.

Preparations suitable for topical administration include liquid or semi-liquid preparations such as liniments, lotions, applicants, oil-in-water or water-in-oil emulsions such as creams, ointments, pastes or gels; or solutions or suspensions.

In addition to the aforementioned ingredients, the preparations of this invention may include one or more additional ingredients such as diluents, buffers, surface active agents, thickeners, lubricants, preservatives, e.g. methyl hydroxybenzoate (including anti-oxidants), emulsifying agents and the like.

The invention will now be further described in the following non-limiting Examples:

EXAMPLE 1

Calcipotriol (2.5 g) was dissolved in ethyl acetate (80 ml) at 50°–80° C. and filtered. The solution was saturated with water, and the product precipitated upon voluntary cooling to room temperature. The resulting slurry was cooled to 0°–10° C. and filtered. The filtered product was dried in vacuo to give calcipotriol, hydrate (2.35 g).

IR spectroscopy KBr technique

Lines characteristic for the hydrate are 1455 (m), 1442 (m), 1330 (w), 1290 (m), 1210 (m), 1085 (m), 907 (m), 895 (m) and 573 (w) $cm^{-1}$, respectively.

Solid state CPMAS[1] NMR The following resonances are characteristic for calcipotriol, hydrate: 147.9, 146.5, 134.8, 130.3, 129.0, 126.5, 116.0, 109.4, 75.5, 68.2, 67.2, 56.9, 55.2, 47.8, 47.5, 42.9, 42.0, 41.3, 30.7, 28.9, 25.6, 23.1, 22.6, 19.5, 14.6, 6.2 and 1.9 ppm, respectively.

Differential Scanning Calorimetry (DSC)

On a Perkin Elmer DSC7 instrument using 20° C./min. and approx. 2 mg sample, the hydrate shows loss of water near 117° C. and a melting peak near 169.7° C.

EXAMPLE 2

Calcipotriol (22.7 g) was dissolved in methanol (200–250 ml), filtered and concentrated in vacuo to a residue which was dissolved in ethyl acetate (200–250 ml) at 50°–80° C. and water (2 ml) was added. The resulting solution was seeded with calcipotriol, hydrate, and the product precipitated upon voluntary cooling to room temperature. Hexane (100 ml) was added from a dropping funnel, the resulting slurry was cooled to 0°–10° C. and filtered.

The filtered product was washed with a 1:1 mixture of ethyl acetate and hexane (200 ml) and dried in vacuo to give calcipotriol, hydrate (19.7 g), shown to be identical with the product described in Example 1.

EXAMPLE 3

Calcipotriol (120 mg) was dissolved in acetone (2 ml) and water (1.5–3 ml) was added. The product crystallized spontaneously and the resulting slurry was cooled to 0°–10° C. and filtered. The filtered product was dried in vacuo to yield calcipotriol, hydrate (100 mg), shown to be identical with the product of Example 1.

EXAMPLE 4

Cream 50 µg/g
Calcipotriol, hydrate . . . 50 mg
Cetomacrogol 1000 . . . 30 g

Cetostearylalcohol . . . 60 g
Chloroallylhexaminium chloride . . . 0.5 g
Propyleneglycol . . . 30 g
Disodiumhydrogenphosphate . . . 2 g
Liquid paraffin . . . 50 g
White soft paraffin . . . 170 g
Purified water . . . up to 1000 g Melt cetomacrogol 1000, cetostearylalcohol, liquid paraffin and white soft paraffin at 75° C. Dissolve propylene glycol in water at 75° C. and mix the solution with the fatty phase. Homogenize the emulsion and cool to 30° C. Mill calcipotriol, hydrate in part of the aqueous phase to a particle size predominantly below 10 μm and suspend in an aqueous solution of disodiumhydrogenphosphate and chloroallylhexaminiumchloride. Add the suspension to the emulsion and fill the cream in tubes.

EXAMPLE 5

Gel 50 μg/g
Calcipotriol, hydrate . . . 52.2 mg (corresponding to 50 mg anhydrous)
Carbomer . . . 7 g
Cetomacrogol 1000 . . . 1 g
Diazolidinyl urea . . . 2 g
Dichlorobenzyl alcohol . . . 1 g
Disodium edetate . . . 0.5 g
Sodium hydroxide . . . 3.7 g
Propylene glycol . . . 30 g
Purified water . . . up to 1000 g Dissolve cetomacrogol, diazolidinyl urea, dichlorobenzyl alcohol, disodium edetate and propylene glycol in water. Add carbomer and homogenize by high speed. Add during agitation sodium hydroxide dissolved in part of the water. Mill the calcipotriol, hydrate in a bottle of water with glass beads until a particle size below 10 μm has been obtained. Add the calcipotriol, hydrate suspension to the gel and mix for 30 minutes. Fill the gel into collapsible tubes.

What we claim is:

1. Calcipotriol monohydrate characterized by its storage stability at 40° C. after 12 months, its ready wettability and wet ball milling characteristics.

2. Pharmaceutical composition containing the compound of claim 1.

3. Pharmaceutical composition according to claim 2 which is a cream.

4. Pharmaceutical composition according to claim 2 which is a gel.

5. Pharmaceutical composition according to any one of claim 4, with a content of the active component of 1–100 μg/g of the composition.

6. The method of preparing calcipotriol monohydrate which comprises dissolving calcipotriol in organic solvent and then adding water to the resulting solution to precipitate the hydrate, said hydrate being characterized by its storage stability at 40° C., its ready wettability and wet ball milling characteristics.

7. In the preparation of a gel formulation which involves wet ball milling a calcipotriol component and adding the wet milled calcipotriol component to a gel base, the improvement which comprises wet milling calcipotriol hydrate as said component and using this wet milled hydrate for addition to said gel base, said hydrate being characterized by its storage stability at 40° C. after 12 months, its ready wettability and wet ball milling characteristics.

* * * * *

UNITED STATES PATENT AND TRADEMARK OFFICE
CERTIFICATE OF CORRECTION

PATENT NO. : 5,763,426
DATED : June 9, 1998
INVENTOR(S) : Erik Torngaard Hansen et al.

It is certified that error appears in the above-identified patent and that said Letters Patent is hereby corrected as shown below:

<u>Title page,</u>
Item [73], Assignee, "Leo Pharmaceutical Products Ltd., Ballerup, Germany" should read -- Leo Pharmaceutical Products Ltd., Ballerup, Denmark --

Signed and Sealed this

Twenty-eighth Day of December, 2004

JON W. DUDAS
*Director of the United States Patent and Trademark Office*